US008944064B2

(12) United States Patent
Akram et al.

(10) Patent No.: US 8,944,064 B2
(45) Date of Patent: Feb. 3, 2015

(54) DEVICES AND METHODS FOR POSITIONING A STEREOTACTIC FRAME

(75) Inventors: Harith Akram, London (GB); Hu Liang Low, Romford (GB)

(73) Assignee: Barking, Havering and Redbridge University Hospitals National Health Service Trust (GB)

( * ) Notice: Subject to any disclaimer, the term of this patent is extended or adjusted under 35 U.S.C. 154(b) by 334 days.

(21) Appl. No.: 13/262,357

(22) PCT Filed: Mar. 30, 2010

(86) PCT No.: PCT/GB2010/000624
§ 371 (c)(1),
(2), (4) Date: Feb. 24, 2012

(87) PCT Pub. No.: WO2010/112843
PCT Pub. Date: Oct. 7, 2010

(65) Prior Publication Data
US 2012/0138066 A1    Jun. 7, 2012

(30) Foreign Application Priority Data
Mar. 30, 2009 (GB) .................................. 0905352.1

(51) Int. Cl.
*A61G 15/00* (2006.01)
*A61B 19/00* (2006.01)

(52) U.S. Cl.
CPC ......... *A61B 19/203* (2013.01); *A61B 2019/207* (2013.01)
USPC ........................................... 128/845; 606/130

(58) Field of Classification Search
USPC ............... 606/54–59, 130; 128/845, 846, 857
See application file for complete search history.

(56) References Cited

U.S. PATENT DOCUMENTS

| | | | |
|---|---|---|---|
| 4,475,550 A | 10/1984 | Bremer et al. | |
| 4,608,977 A * | 9/1986 | Brown | 606/130 |

(Continued)

FOREIGN PATENT DOCUMENTS

| | | |
|---|---|---|
| DE | 869 843 C | 3/1953 |
| WO | 90/13257 A1 | 11/1990 |

OTHER PUBLICATIONS

International Search Report and Written Opinion mailed Jul. 26, 2010 for Application No. PCT/GB2010/000624 (10 Pages).

*Primary Examiner* — Patricia Bianco
*Assistant Examiner* — Tarla Patel
(74) *Attorney, Agent, or Firm* — Fulbright & Jaworski LLP

(57) ABSTRACT

Stereotactic methods are routinely used in neurosurgery for operations such as the aspiration of brain cysts, tumor biopsies and more recently to implant electrodes into brain targets. An integral part of this surgery is a mechanical device called a stereotactic frame (10) that has head holding clamps and bars which puts the head in a fixed position in reference to the coordinate system. Various methods of accurately aligning the frame have been used but a novel device and method are proposed that over-come at least some of the shortcomings of these current techniques. There is disclosed a removable frame attachment (30) that holds the frame in position but allows for fine adjustment, allowing a single operator to quickly and accurately position the frame. The attachment can be removed before surgery without moving the set position of the frame. The device comprises two or more arms (31,32) each arm being coupled to another at a point of intersection. At least one arm comprises a plurality of fixing means (35) and at least one arm is attached to the stereotactic frame (10) using gripping means (33).

15 Claims, 5 Drawing Sheets

(56) References Cited

U.S. PATENT DOCUMENTS

| | | | |
|---|---|---|---|
| 4,638,798 A | * | 1/1987 | Shelden et al. ............... 606/130 |
| 4,706,665 A | * | 11/1987 | Gouda ......................... 606/130 |
| 5,380,336 A | * | 1/1995 | Misko et al. .................. 606/130 |
| 5,728,106 A | * | 3/1998 | Misko et al. .................. 606/130 |
| 5,855,582 A | * | 1/1999 | Gildenberg ................... 606/130 |
| 2002/0042619 A1 | | 4/2002 | Dominguez et al. |

* cited by examiner

DEVICES AND METHODS FOR POSITIONING A STEREOTACTIC FRAME

CROSS-REFERENCE TO RELATED APPLICATIONS

This application is national phase application under U.S.C. §371 of International Application No. PCT/GB2010/000624 filed Mar. 20, 2010, which claims priority to United Kingdom Application No. 0905352.1 filed Mar. 30, 2009, the contents of both of which applications are incorporated herein by reference.

BACKGROUND OF THE INVENTION

Stereotaxy is a method of precisely locating targets in 3-dimensional space using a reference frame. In stereotactic surgery a stereotactic frame is used to determine the coordinates of the target, and then to guide the approach of surgical instruments to that target using a route which results in minimum damage to surrounding tissues.

In theory, any organ system inside the body can be subjected to stereotactic surgery. There are however difficulties in establishing a reliable frame of reference, such as bone landmarks which bear a constant spatial relation to soft tissues. This means that its applications have so far been limited to brain surgery.

In neurosurgery, stereotactic methods are routinely used in operations to aspirate brain cysts, biopsy tumours or delineate the path to deep seated lesions. The main advantage of stereotactic neurosurgery to 'open' brain surgery is the high precision of lesion localisation. The accuracy of target localisation allows operations on lesions deep within the brain to be performed through very small openings. More recently, stereotactic methods have been used to implant electrodes into brain targets. An electrical current is passed through the electrodes to modify brain function and this forms the basis of deep brain stimulation (DBS). DBS is now an accepted neurosurgical treatment used for the management of Parkinson's disease, tremor, dystonia, pain and epilepsy. The potential demand for DBS is great and the numbers of patients undergoing DBS would be even greater if DBS was used for psychiatric and pain procedures and stroke.

One of the major factors determining the success of DBS is the accuracy of electrode placement. This is, in turn, reliant on the accuracy of the method used to determine the target coordinates. The targets are often not much bigger than a grain of rice and in many instances cannot be seen on brain imaging. In these cases the location of the target is calculated relative to a virtual line connecting the anterior and posterior commissure of the brain, the AC-PC line.

The surgery uses a mechanical device called a stereotactic frame that has head-holding clamps and bars which puts the head in a fixed position in reference to the coordinate system (the so-called zero or origin). The stereotactic apparatus uses a set of three coordinates (x, y and z) in an orthogonal frame of reference (Cartesian coordinates), or, alternatively, a polar coordinates system, also with three coordinates: angle, depth and antero-posterior location. It is therefore imperative that the reference frame, i.e. stereotactic frame base upon which the target coordinates are determined, is parallel to the AC-PC line. The AC-PC line runs from the superior surface of the anterior commissure in the brain to the centre of the posterior commissure (Talairach atlas).

There are several different types of stereotactic frames available but the two most commonly employed modern stereotactic frames are the Leksell and the CRW frames from Radionics which are based on the centre-of-sphere concept. These frames comprise of a frame base (or head ring) designed to surround the head in the transverse plane parallel to the AC-PC line. They are made of non ferrous materials such as aluminium so that they can be used with CT and MRI scanners.

A range of attachments are then connected to the frame base, such as head posts, cross bars, arcs and plates. The frame is connected to the patient using self tapping fixing screws that engage with the head posts and are screwed in to the skull. After the frame's fixation, images are taken for preoperative planning. Once localization is completed, the system is prepared for surgery by simply attaching an arc to the frame. The arc is positioned according to the previously calculated X, Y and Z coordinates of the target so its center coincides with the selected cerebral target.

High accuracy of electrode placement during procedures such as DBS is required for the following reasons:
  The target tissue volume is small. If the electrodes are not accurately placed the outcome of surgery is poor.
  In many instances the target is surrounded by other important brain structures. Accurate electrode placement reduces the risk of complications either as a result of electrode placement or due to electrical spread to surrounding structures.
  The DBS procedure is very costly and can take up to 8 hours. A method which could increase the accuracy of electrode placement will not only be clinically beneficial but would have financial implications as well.

The initial part of deep brain stimulation surgery involves the attachment of the stereotactic frame to the skull parallel to the AC-PC line. The stereotactic frame is first placed around the head and the base (head ring) of the stereotactic frame is aligned with the AC-PC line. Four screws are then passed through head posts attached to the frame base and these screws are attached to the skull under local anaesthetic.

Various methods have been used to align the frame including the use of plastic bars attaching the frame to the ear canals, connecting the frame base across the top of the head with extensible tape or using several people to help align the frame by visual inspection. These methods have the following shortcomings:
  They are uncomfortable to the patient.
  They do not readily allow fine adjustment to frame position.
  They are relatively labour intensive, i.e. requires two or more assistants that are quite likely to be highly paid clinicians.
  The process can be very time consuming and if not completed promptly it can delay the surgical procedure, which could lead to a myriad of problems for the patient and operational running of the surgery.
  They do not allow easy removal and re-application.
It is an object of the invention to at least partially address one or more of the above problems.

BRIEF SUMMARY OF THE INVENTION

According to an aspect of the invention, there is provided a device for positioning a stereotactic frame relative to a person's head, the device comprising: two or more arms, each arm being coupled to another arm at a point of intersection, at least one arm comprising a plurality of fixing means adapted to engage a person's head, and wherein at least one arm is adapted to receive and hold a stereotactic frame.

The device allows the frame to be positioned quickly and easily. Preferably, the device is arranged so that it can be reversibly attached to the stereotactic frame, to be removed once the screws are inserted to fix the frame in position, for example.

Tests have shown that the degree of deviation off the AC-PC line on MRI confirmed images when the present invention is used to position the stereotactic frame is of the order of 2 mm or less in the sagittal plane (the imaginary plane that travels from top to bottom of the body, dividing it equally into left and right portions). There is commercially available image manipulation software that enables the surgeon to calculate the target coordinates relative to the AC-PC line even when the alignment of the stereotactic frame to the AC-PC line is far from ideal. However, it is universally agreed that the accuracy target determination, even with the use of software, is improved if the frame is appropriately aligned with the AC-PC line. Moreover, the inherent error in using a mathematical algorithm to correct for a badly positioned frame cannot be completely removed.

The present invention is designed primarily for positioning the stereotactic frame for stereotactic functional neurosurgery. However, it can be used for any form of stereotactic brain surgery including radiosurgery.

BRIEF DESCRIPTION OF THE DRAWINGS

The invention will be more clearly understood from the following description, given by way of example only, with reference to the accompanying drawings, in which.

DETAILED DESCRIPTION

Figure 1:
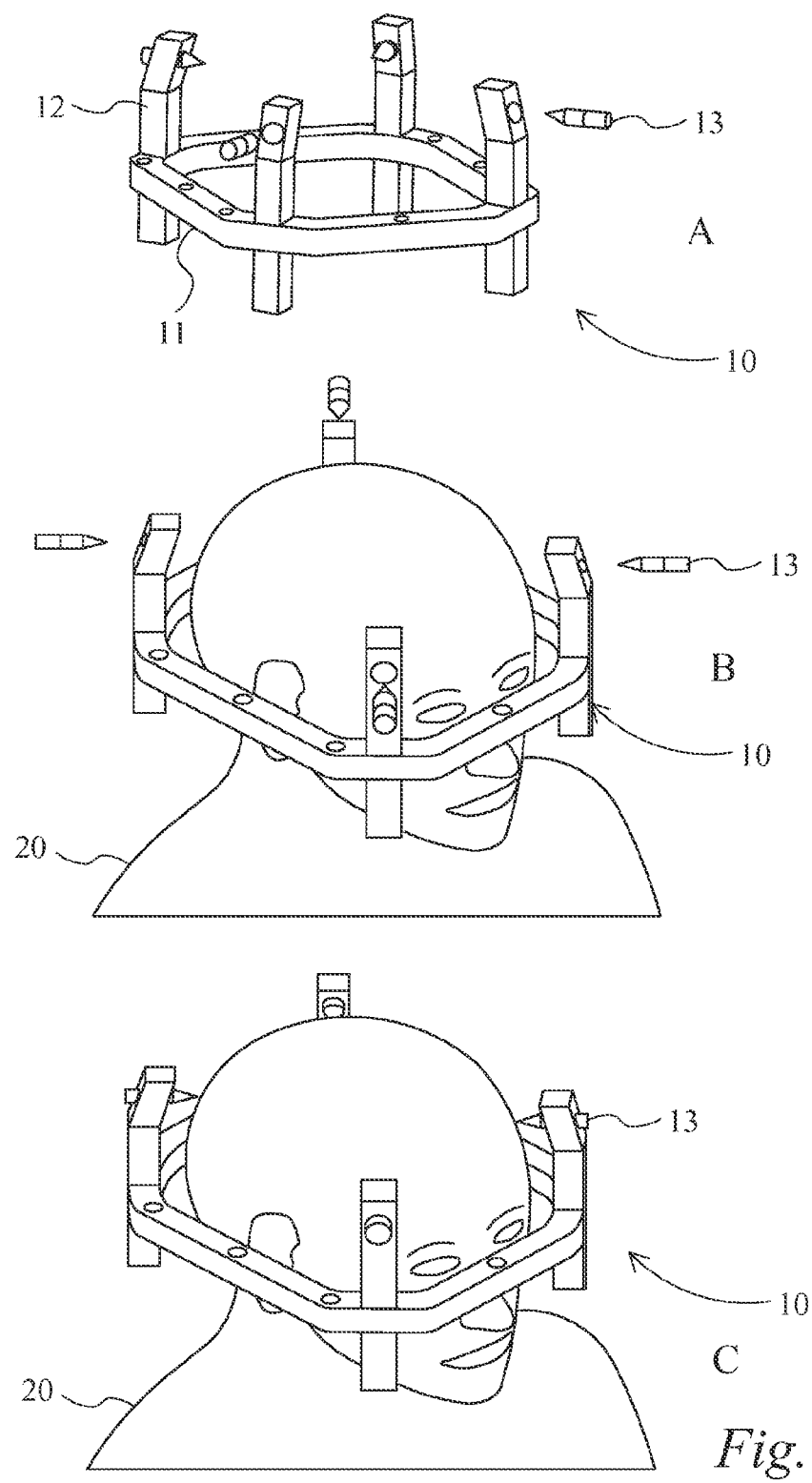
FIG. 1 depicts a standard stereotactic frame and the fixation technique to the head of a person.

The use of arrangements disclosed in this application have several advantages, including but not limited to the following:

The device of the present invention makes it easier and quicker to position the frame. According to an embodiment, the device uses an attachment arrangement that can be reversibly attached to the most widely used frames, including the CRW frame and the Leksell frame.

The device only comes into contact with the scalp via temporary fixing means so that it does not cause discomfort.

According to an embodiment, the device allows the surgeon to make both gross and fine corrections to the frame angle before the frame is screwed onto the skull. The ability to make small adjustments is particularly important as fine-tuning the position of the frame with most commercially available devices is often difficult and time consuming.

The fixing screws that connect the stereotactic frame to the skull are inclined medially and upwards for all commercially available stereotactic frames. The presently available stereotactic frame positioning aids allow alignment of the frame with the skull before the fixing screws are inserted. However, the frame position may deviate as the fixing screws are tightened due to the way the latter are orientated. This could affect the position of head relative to the centre of the frame. The only way to correct this once the fixing screws have been tightened is to remove the frame and start again. This is both painful for the patient and time consuming. According to an embodiment of the present invention, the device allows the surgeon to make small frame position adjustments to mimic the action of the fixing screws during tightening thereby predicting the final position of the frame relative to the head. The surgeon can then factor this into his calculations when aligning the frame to the skull.

The device can hold the stereotactic frame to the head (before fixing screws are inserted) and allow gross and fine adjustments to be made by only one person.

The time required to apply a stereotactic frame, align it to the AC-PC line and secure it to the skull is reduced mainly because fewer trial applications are required. On average, the application time is approximately 15 minutes or less.

The disclosed devices can be attached and removed easily and quickly. This allows the surgeon to use the devices to position a stereotactic frame on a patient's head on the ward. The proposed final position of the frame can then be marked on the patient's scalp with an indelible marker. When the patient arrives in the operating room, the stereotactic frame can be secured to the skull by just aligning the frame screws with the points marked on the patient's scalp. This significantly speeds up the operating time.

The arms of the device are adapted to place the fixing means against the head. In one aspect, the arms are preferably arched or curved. It is preferred that the arch or curve follows loosely the outline of the head of a person, to enable the fixing means to be temporarily placed into contact with the head. In one aspect, the arms are substantially semi circular or a part thereof. Alternatively, the arms are in a partial ovoid or elliptical shape. The arms may be any suitable length, and need not traverse the entire top of the head in order for the device to function.

The arms are preferably composed of a solid material, such as a plastic or metal. As the device is removed before the patient is placed in the CT or MRI scanner the device can be made from a different material to the frame, these materials could include, but are not limited to, polystyrene, PVC, PU, Nylon, PTFE, aluminium or steel. The material from which the arms are made may be flexible or rigid. Preferably, the material has sufficient flexibility to allow the device to be fitted against the head of the user whilst providing sufficient structure to support the stereotactic frame without undue movement. Thus, in a preferred embodiment, the arms of the device have a limited degree of flexibility.

In the present invention, two or more arms are present. The arms are arranged to support a stereotactic frame against the head of a person, in order to fit the frame to the skull accurately. At least one arm may thus be arranged to traverse the top of the head in any direction, to engage with the stereotactic frame. Each arm of the device may be designed to traverse a different part of the head, for example in a preferred embodiment, the device has two arms. The first arm may traverse the head from ear to ear, across the top of the head (generally in line with the coronal plane which divides the body into equal dorsal and ventral portions). The second arm may traverse the top of head from front to back (generally in line with the sagittal plane). It will be understood by the skilled person that the arms may deviate substantially from these planes and not affect the functioning of the present invention.

Each arm of the present invention intersects with at least one other arm in order to provide a stable structure in order to support the stereotactic frame. At the point of intersection, the arms are coupled. This coupling may be fixed (immoveable or permanent) or allow a range of movement between the arms. For example, the coupling may be a pivot, a ball joint, sliding rule or hinge. Movement at the point of intersection and coupling may be desirable in order to enhance the user's ability to fit the device of the present invention to the head of a person. If movement is permitted at the coupling, there may also be provided means for immobilizing that movement.

A securing means may be provided at the coupling, such as a pin or a grip, to prevent further movement once the desired fit had been achieved. In a preferred embodiment, the fixing means is adapted to also act as a securing means at the coupling. However, in a preferred embodiment, the arms are coupled at the point of intersection in a fixed manner.

The point at which the arms intersect may be at any point along their length. Preferably, the arms intersect at a point which is substantially at the middle of the length, such that the coupling supports the device on the top of the head. However, the arms may intersect at any point, and for example may be coupled at their ends.

In a preferred embodiment, the device has two arms. Preferably one arm traverses the head substantially in line with the sagittal plane, and the other substantially in line with the coronal plane. The arms are thus designed to intersect substantially perpendicularly. The arms may intersect at a point along their length which is substantially central. In this configuration, the arms intersect and form a cross-like configuration. This provides support for the frame across the upper surface of the head and thus prevents forwards/backwards and side-to-side movement whilst adjusting the fit of the frame. It will be understood that this device could be used in many orientations on the head, and does not need to be in line with particular planes. It is preferred that the arm which is adapted to receive and hold the frame traverses the head in the coronal plane (essentially from ear-to-ear) but this is not obligatory. In a preferred embodiment, the arm which traverses the head from front to back (sagittal plane) is shorter, as it is not required to receive and hold the stereotactic frame. In some embodiments, this arm may also be adapted to receive and hold the frame. Alternatively, this configuration can be achieved using 4 arms that intersect and are coupled at their ends at the centre of the cross-like configuration.

It will be appreciated by a person skilled in the art that alternative embodiments of the invention can provide similar support for the stereotactic frame. For example, in one embodiment, the device may comprise 4 arms, two of which that traverse the head from side to side, and the other two which traverse the head from front to back. In this arrangement, the arms would each intersect with two other arms.

In order to support the stereotactic frame, the device needs to be attached to the frame in a suitable manner. This attachment needs to be reversible without causing the stereotactic frame to move. At least one of the arms is adapted to receive and hold the stereotactic frame. In order to support the frame, it is desirable that the device attaches to the stereotactic frame in at least two places. Preferably, both ends of one arm of the device are adapted to receive and hold the frame. However, two arms may both be adapted to receive and hold the stereotactic frame in an alternative embodiment, with one or both ends of these arms being adapted.

It is preferred that the device is arranged to receive and hold the stereotactic frame at a point on the lateral section of the frame. Thus, the arm(s) that is adapted to receive and hold the frame traverses the head from side-to-side.

In order to receive and hold the device, the arm(s) is adapted. This adaptation may take any suitable format. In a preferred embodiment, the adaptation allows the arm to grip or clip onto the stereotactic frame. In an alternative embodiment, the adaptation allows the arm or part thereof to fit within a receiving means which is part of the frame, or attached to the frame.

For example, several devices are available that attach to the stereotactic frame in order to complete certain procedures. In all embodiments, the device is designed such that it may be released without causing any movement of the stereotactic frame. To enable this, a release means may be incorporated into the device, or in the receiving means attached to the stereotactic frame.

In one embodiment, the receiving means may be attached to the stereotactic frame, and at least one arm of the device may be adapted to receive and hold the frame via the receiving means. In this embodiment, the ends of the arm may be adapted by being able to slot within the receiving means. The two elements may be held together using a pin or similar whilst the device and frame are being adjusted. When the required fit has been made, the pin can be removed, and the device lifted from the head without causing movement of the frame.

In an alternative embodiment, at least one arm of the device may be adapted to receive and hold the frame by the presence of a gripping mechanism. This gripping mechanism may be released without causing movement of the frame. For example, the gripping mechanism can be made from a flexible material or have a release mechanism present.

The device further comprises a plurality of fixing means which are adapted to engage a person's head. These fixing means are preferably adjustable and fix the device to the person's head in a temporary manner. In a preferred embodiment, pluralities of fixing means are present on at least one arm of the device. Preferably, pluralities of fixing means are present on each arm of the device. More preferably, pluralities of fixing means are present along the length of each arm. The fixing means may be integral and permanently fixed to each arm, or they may be detachable.

The fixing means are applied to the head of a person in order to fix the device temporarily in place. In a preferred embodiment, the fixing means are screws, most particularly adjustable screw actuators. Such screws may be threaded through appropriate sized apertures in the arms, and be adjusted such that the device sits against the head of a person. It is preferred that the tip of the screw is cushioned or soft. Preferably the tip of the screw is made from rubber or similar, or is padded. Such embodiments increase the comfort of the device in use. By adjusting the screws, the user can fit the device against the person's head, providing a secure support for the stereotactic frame.

By turning the screws, the stereotactic frame can be adjusted in the x-, y- and z-planes so that the stereotactic frame base is positioned parallel to the AC-PC line. It will be understood by the skilled person that there are a wide range of actuators that could be used instead of the screw actuators. This would comprise linear actuators that include, but are not limited to, mechanical, electric, pneumatic, hydraulic and piezoelectric actuators. It would also be possible to employ motors that would use rotary motion to create a linear activation using an appropriate mechanical arrangement.

There may also be provided a method of positioning a stereotactic frame on the head of a person, comprising use of a device for positioning a stereotactic frame relative to a person's head, the device comprising: two or more arms, each arm is coupled to another arm at a point of intersection, at least one arm comprising a plurality of fixing means adapted to engage a person's head, and wherein at least one arm is adapted to receive and hold a stereotactic frame. The method is discussed in more detail below.

Preferred embodiments of the invention will now be discussed in more detail, with particular reference to the figures.

FIG. 1 depicts the positioning of the stereotactic frame (10) and attachment to the head of the person (20). FIG. 1A shows that the frame (10) is composed of a frame base (11) that is positioned parallel to the AC-PC line, four head posts (12) positioned around the head, and four fixing screws (13) that go through the posts and fix the skull to the frame (10) in the correct position. FIG. 1B shows the insertion of the screws (13) into the head posts (12). FIG. 1C shows how these screws (13) penetrate the skull of the person (20).

Figure 2:
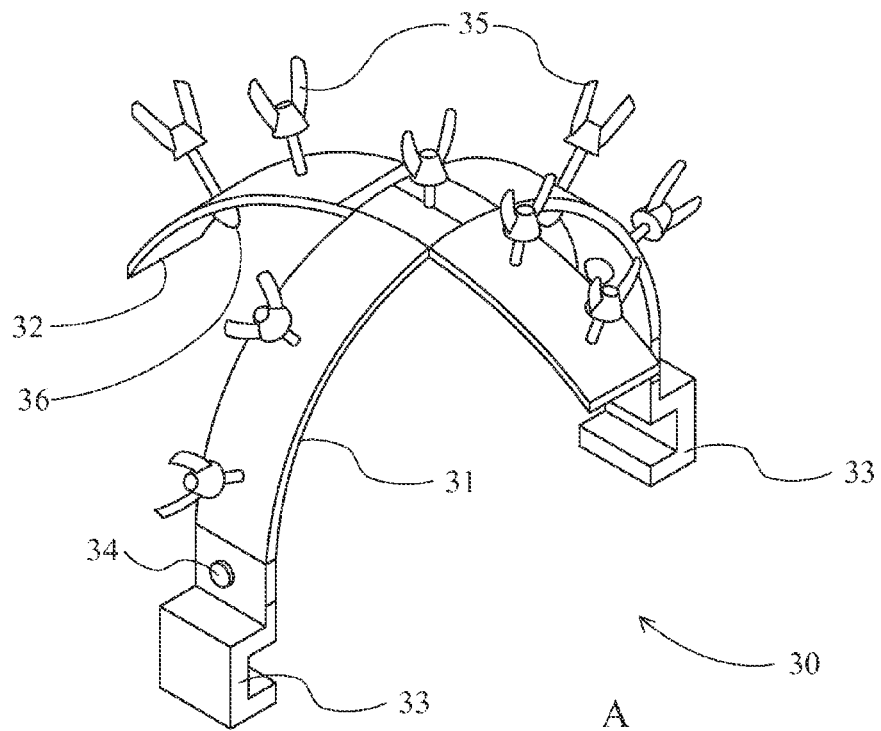
FIG. 2 depicts a preferred embodiment of the invention, on its own (A), or in conjunction with a stereotactic frame (B)
Figure 2:
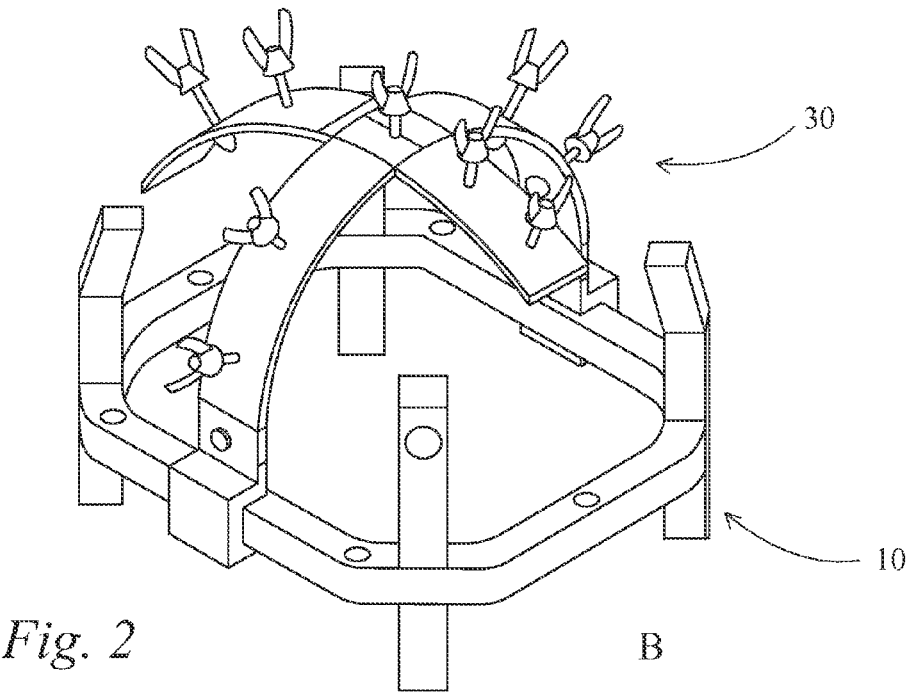

A device according to an embodiment of the invention (30) and its attachment to the frame is shown in FIGS. 2A and 2B. In this embodiment of the invention, the device (30) in FIG. 2A has two perpendicularly intersecting arms (31, 32) with a series of fixing means (35) in both arms. The holder is attached to the lateral section of the frame (10) in FIG. 2B using a gripping means (33). This figure shows one possible embodiment of the device but it is possible to have a universal grip mechanism that will fix the holder to a wide range of frames. There is also a pin (34) that allows the arm adapted to receive and hold the frame (31) to be temporarily fixed to the gripping means (33) allowing easy removal of the device once the frame has been fixed into position.

Figure 3:
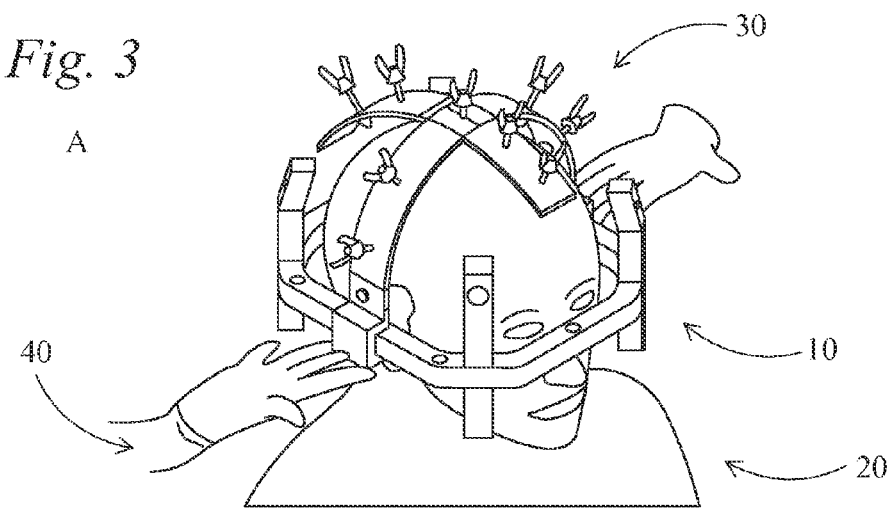
FIG. 3 depicts a preferred embodiment of the invention in use with a stereotactic frame on the head and adjusted to the correct position.
Figure 3:
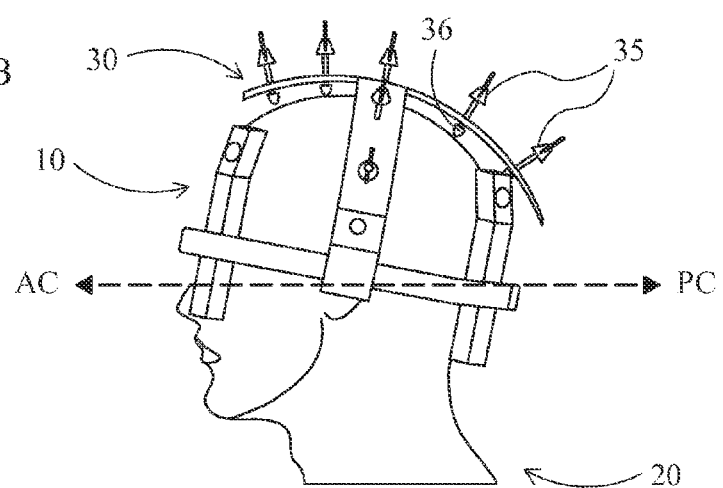
Figure 3:
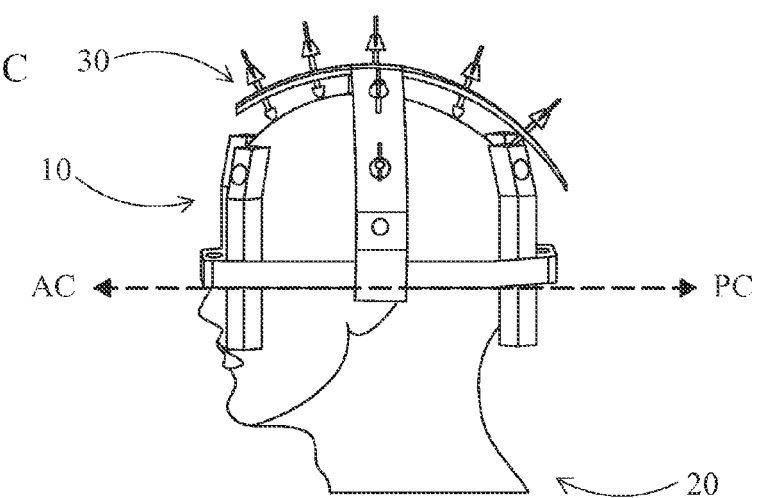

A method for placing the frame using a device according to an embodiment of the present invention on the head of a person is shown in FIG. 3. FIG. 3A depicts a preferred embodiment of the device of the present invention (30), which is attached to the frame (10) and placed on to the head of a person (20) by hand using a single operator (40). FIG. 3B shows that the device rests on the head of the patient via the padded ends (36) of the fixing means (35) of the device (30). The operator is free to take their hands off the device, rather than having to hold the device at all times or getting someone else to hold the frame in place.

When the device is first placed on the head it is unlikely to be in the correct position relative to the AC-PC line, shown in an exaggerated manner in the figure. The operator/user can now adjust the frame as required, initially by gross movement of the frame and holder and then by fine adjustment of the fixing means (35), which are preferably screw actuators. As the frame is held in position there is no chance of the operator/user 'dropping' the frame and having to start again, particularly important as their arms may get tired during the alignment procedure, which is not quick.

It is also known that many of the patients undergoing the procedure will have movement disorder, such as Parkinson's disease, which can make alignment very difficult without a frame holder. FIG. 3C shows the frame (10) placed in the correct alignment on the head of a person (20), with reference to the AC-PC line.

Figure 4:
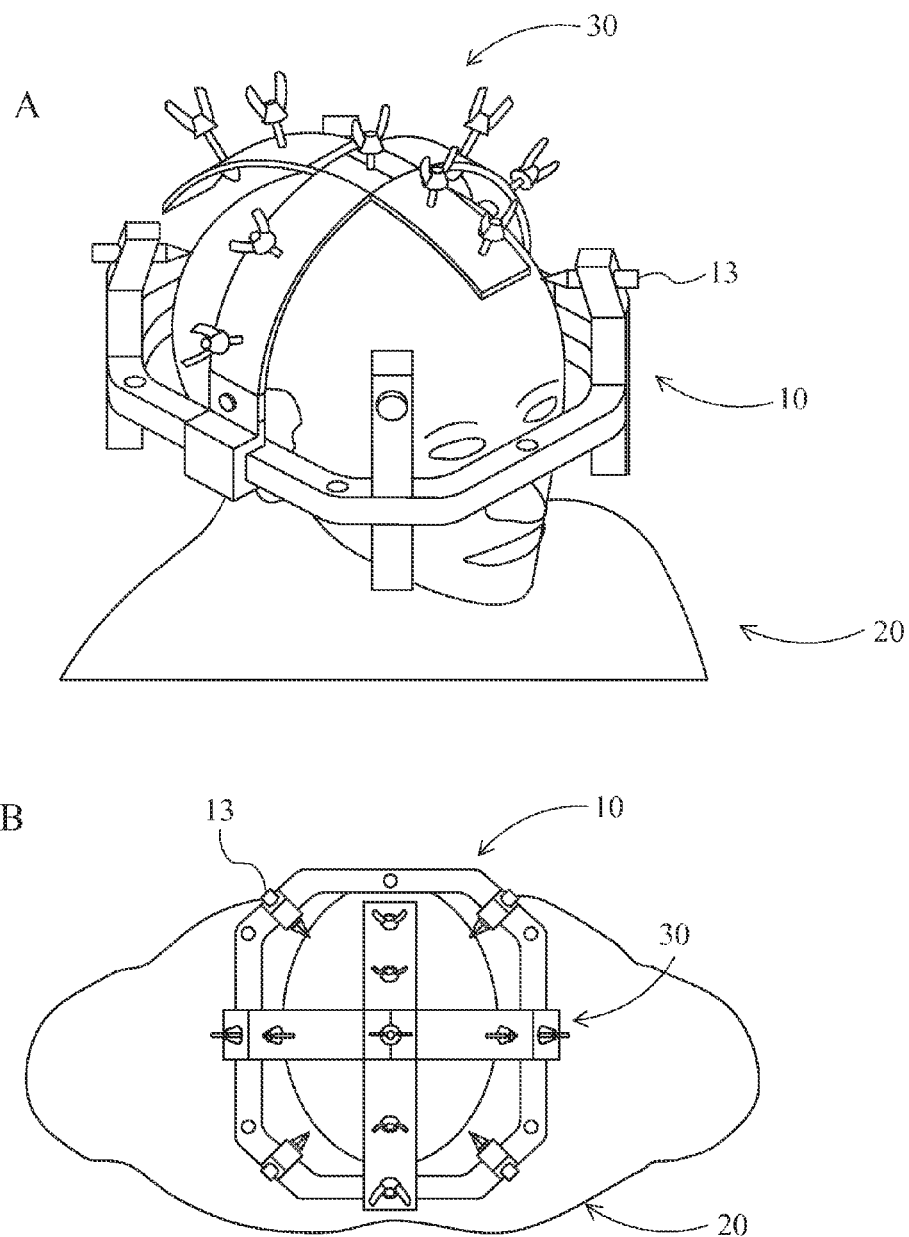
FIG. 4 depicts a preferred embodiment of the invention whereas the frame is in the correct position and the frame screws have been inserted. Views are isometric (A) and from above (B)

Once the frame (10) is in the desired location the frame fixing screws (13) can be inserted into the skull of the person (20) to hold the frame (10) in position, as shown in FIGS. 4A and B. FIG. 4A depicts an isometric view and FIG. 4B the view from above.

Figure 5:
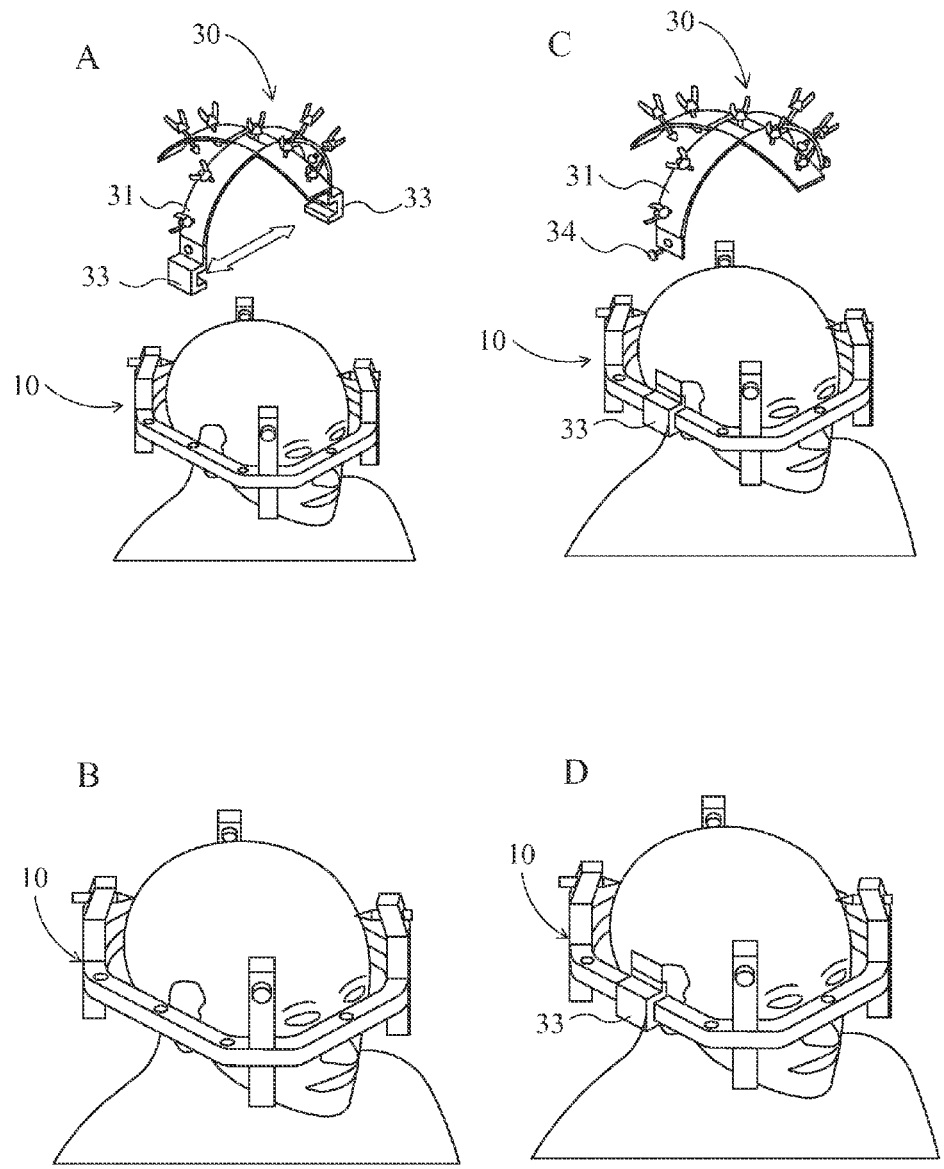
FIG. 5 depicts two attachment/release means for a preferred embodiment of the invention.

Once the frame (10) is securely fixed in position via the screws (13), the device of the present invention (30) may be removed before the surgical procedure, as shown in FIG. 5. The figure shows two alternative embodiments of the invention. In the first embodiment (FIGS. 5A and 5B) the entire device (30) is removed by simply removing the gripping means (33) from the frame (10). In this embodiment, the gripping means could be made from a flexible material, or have a release mechanism that opens the grip. In the second embodiment the arm (31) which is adapted to receive and hold the frame (10) is detached from the gripping means (33) using a pin (34), this leaves the gripping means in place following placement of the frame (10). Ideally, therefore, the gripping means should be made from a non-ferrous material, as they would be present during surgery.

With the holder removed and the frame in the correct position the stereotactic procedure can begin.

The invention claimed is:

1. A device for positioning a stereotactic frame relative to a person's head, the device comprising:
   two or more arms, each arm being coupled to another arm at a point of intersection, at least one arm carrying a plurality of adjustable actuators adapted to engage a person's head such that the adjustable actuators are each inclined medially and upwards with respect to the person's head;
   wherein at least one arm is adapted to receive and hold a stereotactic frame; and
   wherein the plurality of adjustable actuators are adjustable to change position of the stereotactic frame with respect to the person's head in lateral, anterior-posterior, and inferior-superior directions.

2. The device of claim 1 wherein at least one of the two or more arms is arched or curved and arranged to follow the outline of the person's head substantially in line with the sagittal plane.

3. The device of claim 2 wherein two of the two or more arms are configured such that when the device holds the stereotactic frame, the two arms are arranged in a substantially cross-like configuration.

4. The device of claim 1 wherein a coupling between the two or more arms allows movement between at least two of the two or more arms.

5. The device of claim 1 wherein the adjustable actuators are configured to be adjustable to mimic the action of a plurality of a fixing screws carried by the stereotactic frame.

6. The device of claim 1 wherein the adjustable actuators comprise screws.

7. The device of claim 6 wherein the adjustable actuators are soft-tipped.

8. The device of claim 1 wherein the adjustable actuators are present along a length of the arms.

9. The device of claim 1 wherein at least one of the two or more arms is adapted to receive and grip a stereotactic arm.

10. The device of claim 1 wherein at least one of the two or more arms is adapted to receive and grip a stereotactic frame.

11. A method comprising:
    positioning a device for holding a stereotactic frame on the head of a person, the device comprising a plurality of adjustable actuators adapted to engage the head of a person such that at least one of the adjustable actuators is inclined medially and upwards with respect to the head of the person to mimic the action of a fixing screw carried by the stereotactic frame, wherein the plurality of adjustable actuators are adjustable to change position of the stereotactic frame with respect to the person's head in lateral, anterior-posterior, and inferior-superior directions;

adjusting at least one of the actuators to select a position of the stereotactic frame to the device with respect to the head of the person; and fixing the stereotactic frame to the head of the person in the position selected using the actuators.

12. The method of claim 11, wherein in the positioning step the device rests on the head of the person via the adjustable actuators in a stable manner, such that if an operator removes his hands from the device the device remains in engagement with the head of the person.

13. The method of claim 11, further comprising:

adjusting the adjustable actuators to align the stereotactic frame relative to the head prior to fixing the stereotactic frame to the head of the person, marking a scalp of the head of the person to identify the position of the fixing screw carried by the stereotactic frame.

14. The method of claim 11, further comprising:

attaching the stereotactic frame to the head of the person; and after the adjusting step, removing the device while leave the stereotactic frame attached to the head of the person.

15. A device for positioning a stereotactic frame relative to a person's head, the device comprising:

two or more arms for supporting a stereotactic frame, each of the arms being coupled to another of the arms at a point of intersection;

a plurality of adjustable fixing means carried by at least one of the arms, the adjustable fixing means adapted to fix the device in place by engaging a person's head such that at least one of the adjustable fixing means is inclined medially and upwards with respect to the person's head;

wherein at least one of the support means is adapted to receive and hold a stereotactic frame; and wherein the plurality of adjustable fixing means are adjustable to change the position of the stereotactic frame can be relative to the person's head in a lateral, anterior-posterior, and inferior-superior directions.

* * * * *

UNITED STATES PATENT AND TRADEMARK OFFICE
CERTIFICATE OF CORRECTION

| | | |
|---|---|---|
| PATENT NO. | : 8,944,064 B2 | Page 1 of 1 |
| APPLICATION NO. | : 13/262357 | |
| DATED | : February 3, 2015 | |
| INVENTOR(S) | : Harith Akram et al. | |

It is certified that error appears in the above-identified patent and that said Letters Patent is hereby corrected as shown below:

In the Claims

<u>Claim 15, Column 10, Line 16:</u>

Delete "can be".

Signed and Sealed this
Eleventh Day of August, 2015

Michelle K. Lee
*Director of the United States Patent and Trademark Office*